United States Patent

Nguyen

Patent Number: 5,118,444
Date of Patent: Jun. 2, 1992

[54] AQUEOUS AGRICULTURAL COMPOSITIONS EXHIBITING REDUCED IRRITATION AND CORROSION

[75] Inventor: Giao V. Nguyen, Lewisville, Tex.

[73] Assignee: Witco Corporation, New York, N.Y.

[21] Appl. No.: 683,313

[22] Filed: Apr. 10, 1991

[51] Int. Cl.$^5$ ............... A61R 35/78; C09K 15/20
[52] U.S. Cl. ............... 252/390; 252/387; 252/392; 71/DIG. 4; 424/195.1
[58] Field of Search ............... 252/387, 390, 392; 71/DIG. 4; 424/195.1

[56] References Cited

U.S. PATENT DOCUMENTS

| | | | |
|---|---|---|---|
| 3,121,750 | 2/1964 | De Groote et al. | 260/584 |
| 3,799,758 | 3/1974 | Franz | 71/86 |
| 3,853,530 | 12/1974 | Franz | 71/76 |
| 4,420,414 | 12/1983 | Valone | 252/392 |
| 4,528,023 | 7/1985 | Ahle | 71/86 |
| 4,759,908 | 7/1988 | Incorvia | 422/14 |

FOREIGN PATENT DOCUMENTS 61-122208 6/1986 Japan.

OTHER PUBLICATIONS

Zamer, Chem Abstracts 84:20 136647h p. 47 Adhesives Comprising Solutions of a Mixture of a Terpene . . .
Doerr, Chem Abstracts 101:12 93084x Use of Amine Oxides in Pulp and Paper Production.
Lion Corp. Chem Abstracts 104:2 7517y. Dry Cleaning Compositions.
Chiba Chem Abstracts 106:17 133821x Stabilized Insecticides.
Wedler, Chem Abstracts 108:11 94034n Preparation and Some Properties of Amine Oxides . . .
Klopoter, Chem Abstracts 110:21 192246u Preparation of 3-(N,N-polyoxyethyleng-N-Alry . . .

*Primary Examiner*—Ronald W. Griffin
*Assistant Examiner*—Ralph Gitomer
*Attorney, Agent, or Firm*—Lockwood, Alex, FitzGibbon & Cummings

[57] ABSTRACT

The present invention discloses a method of producing as aqueous agricultural composition exhibiting reduced irritation to animals and corrosiveness to materials by admixing an agriculturally acceptable pesticide and an amine-oxide surfactant having the Formula:

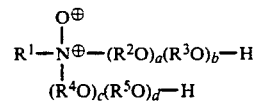

wherein $R^1$ is a straight or branched chain about $C_6$ to about $C_{20}$ alkyl or alkenyl group, $R^2$, $R^3$, $R^4$ and $R^5$ are each independently selected from the group of straight and branched chain lower alkylenyl groups, and $a+b+c+d$ is about 5 to about 25. The compositions exhibit reduced eye irritation to animals and reduced corrosiveness to metals. A method of treating plants is also disclosed.

13 Claims, No Drawings

AQUEOUS AGRICULTURAL COMPOSITIONS EXHIBITING REDUCED IRRITATION AND CORROSION

TECHNICAL FIELD

This invention relates to a method of producing an aqueous agricultural composition exhibiting reduced irritation to animals and reduced corrosiveness to materials by admixing an agricultural compound with an amine-oxide surfactant that exhibits reduced irritation and corrosiveness. Preferably, the agricultural compound is a herbicidally active compound.

BACKGROUND OF THE INVENTION

Many agricultural compounds such as herbicides, fertilizers, pesticides and the like must be absorbed to be effective. For example, herbicides are utilized to inhibit or destroy plant growth.

A compound that enhances the absorption of agricultural compounds such as herbicides is a tertiary amine surfactant having the Formula:

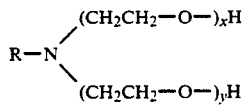

where R is derived from tallow oil having an average of 18 carbon atoms and $x+y$ total 15.

However, these surfactants are irritants to animals and corrosive to materials. It is presently believed that the irritative and corrosive effects are due to the unshared pair of electrons in the amino group. The amine can be neutralized with an organic or inorganic acid, e.g., acetic acid, that converts the amino group to its ammonium derivative. However, neutralization with these organic or inorganic acids does not satisfactorily reduce the irritative or corrosive effect of the surfactant or the composition to which it is added.

SUMMARY OF THE INVENTION

This invention is directed to a method of producing an aqueous agricultural composition exhibiting reduced eye irritation to animals and reduced corrosiveness to metals comprising admixing an agriculturally acceptable pesticide with an amine-oxide surfactant of the Formula I:

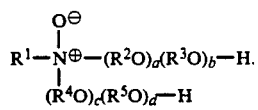

wherein $R^1$ is a straight or branched chain about $C_6$ to about $C_{20}$ alkyl or alkenyl group, $R^2$, $R^3$, $R^4$ and $R^5$ are each independently selected from the group of straight and branched chain lower alkylenyl groups, and $a+b+c+d$ is about 5 to about 25. Preferably, $a+c$ is about 5 to about 15 and $b+d$ is 1 to about 10.

Agriculturally acceptable pesticides include herbicides, insecticides, fungicides and biocides.

The amine-oxide surfactant of Formula I can be produced by oxidizing a tertiary amine surfactant having the Formula II:

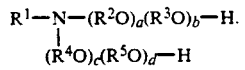

wherein $R^1$, $R^2$, $R^3$, $R^4$, $R^5$, a, b, c and d are as described above.

This invention is also directed to an aqueous agricultural composition comprising an agriculturally acceptable pesticide admixed with an amine-oxide surfactant of Formula I. The compositions of the present invention exhibit reduced eye irritation to animals and reduced corrosiveness to metals compared to conventional compositions.

This invention is also directed to a method of treating plants comprising the step of applying the aqueous agricultural composition to the plant.

DETAILED DESCRIPTION OF THE PREFERRED EMBODIMENTS

The method of the present invention produces an aqueous agricultural composition exhibiting reduced eye irritation to animals and reduced corrosiveness to metals. The method comprises admixing an agriculturally acceptable pesticide with an amine-oxide surfactant of the Formula I:

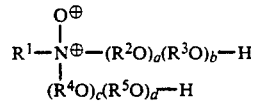

wherein $R^1$ is a straight or branched chain about $C_6$ to about $C_{20}$ alkyl or alkenyl group, $R^2$, $R^3$, $R^4$ and $R^5$ are each independently selected from the group of straight and branched chain lower alkylenyl groups, and $a+b+c+d$ is about 5 to about 25. Preferably, $a+c$ is about 5 to about 15 and $b+d$ is 1 to about 10.

Representative alkyl and alkenyl groups include hexyl, octyl, decyl, dodecyl, tetradecyl, hexadecyl, and octadecyl groups, their unsaturated counterparts and the like.

Preferably, $R^1$ is a straight or branched chain about $C_8$ to about $C_{18}$ alkyl or alkenyl group that can be derived from a fatty acid such as tallow acid, coconut acid, soya acid, cottonseed acid, lauric acid and stearic acid.

Representative lower alkylenyl groups include $C_2$ to about $C_4$ alkylenyl groups, e.g., ethylenyl, propylenyl, butylenyl and the like. Preferred lower alkylenyl groups include ethylenyl, 1,2-propylenyl, 1,2-butylenyl and 2,3-butylenyl.

Preferably, $R^2$, $R^3$, $R^4$ and $R^5$ are each independently selected from the group of straight and branched chain $C_2$ and $C_3$ alkylenyl groups. Most preferably, $R^2$ and $R^4$ are alike, $R^3$ and $R^5$ are alike and $R^2$ and $R^4$ can be the same as, or different from, $R^3$ and $R^5$.

One of a and b can be 0 and one of c and d can be 0. Preferably, $a+b+c+d$ is about 5 to about 20.

Representative commercially available surfactants of Formula II include:

ETHOXYLATED TALLOWAMINES SUCH AS:
FLOMO TA-10, TA-15, TA-20 from DESOTO INC.,
VARONIC T-205, T-210, T-215 from SHEREX,
ETHOMEEN T/12, T/15 from ARMAK CHEMICAL, ALKAMINOX T-10, T-15 from ALKARIL CHEMICALS;
ETHOXYLATED COCOAMINES SUCH AS:
VARONIC K-205, K-210, K-215 from SHEREX
ETHOMEEN C/12, C/15 from ARMAK CHEMICAL,
ACCOMEEN C10, C15 from CAPITAL CITY PRODUCTS,
CHEMEEN C5, C10, C15 from CHEMAX; and
ETHOXYLATED SOYAAMINES SUCH AS
ACCOMEEN S5, S10 from CAPITAL CITY PRODUCTS,
ETHOMEEN S/12, S/15 from ARMAK CHEMICAL
MAZEEN S2, S5 from MAZER CHEMICALS, and
PEGAMEEN S5, S20, from BORG-WARNER CHEMICAL.

The surfactant of Formula I can be produced by oxidizing a tertiary amine surfactant having the Formula II:

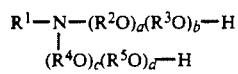

$$R^1-N-(R^2O)_a(R^3O)_b-H$$
$$\phantom{R^1-N-}(R^4O)_c(R^5O)_d-H$$

wherein $R^1$, $R^2$, $R^3$, $R^4$, $R^5$, a, b, c and d are as described above.

A conventional, strong oxidizing reagent is utilized to oxidize the tertiary amine surfactants of Formula II to produce the amine-oxide surfactants of Formula I. An oxidation reaction described in March, "Advanced Organic Chemistry," 3rd Edition, Wiley-Interscience, 1985, p. 1088 can be used to prepare the compounds of Formula I.

Representative oxidizing reagents include hydrogen peroxide, per-acids, the like and mixtures thereof.

Representative per-acids include persulfuric acid, perchromic acid, peracetic acid and the like.

Peracids must be converted (in situ) into their salts to be effective, since these acids would neutralize the tertiary amine via the acid-base reaction, and thus prevent the oxidation from occurring.

If peracids are to be used as the oxidizing agents, the oxidation process would involve the careful, slow addition of the peracids to a mixture of tertiary amine and a strong alkaline, such as sodium hydroxide.

Salts of peracids can also be used as oxidizing agents. Representative salts are the sodium, potassium and ammonium salts. Preferred per-acid salts are sodium perborate and sodium percarbonate. When being added to the mixture of tertiary amine and water, these oxidizing agents would first react with water to yield hydrogen peroxide in which, in turn, would oxidize the tertiary amine to result in the N-oxide product.

A preferred oxidizing reagent is hydrogen peroxide because the by-product of the oxidation reaction is water which does not have to be removed. Although hydrogen peroxide is commercially available in many concentrations, it is preferably utilized as an aqueous solution having a concentration in the range of about 35 to about 50 weight percent (wt %) to achieve a relatively fast reaction that is easily controlled.

The amount of oxidizing reagent utilized to oxidize the tertiary amine surfactant of Formula II depends upon the strength of the oxidizing reagent. Preferably, the amount of oxidizing reagent is selected to oxidize about 90 to about 100, more preferably about 95 to about 100, percent of the amino groups.

The oxidation of the tertiary amine surfactant of Formula II is performed in a suitable reactor that can be a glass, glass-lined or stainless steel reactor. The reactor is preferably equipped with an internal agitator, a heating device capable of raising the temperature of the contents of the reactor, a cooling device to enable a quick reduction in the temperature of the contents of the reactor, and a temperature control device to maintain the temperature of the contents of the reactor at a desired level.

In the oxidation process, the tertiary amine of Formula II (1 mole) is introduced into the reactor. Agitation is initiated and maintained throughout the process, and the contents of the reactor are preheated to a temperature of about 75° C. (167° F.). To facilitate the control of the reaction, oxidizing agent (1.5-2.5 moles) is introduced into the reactor in two portions; the major portion, consisting of about 60-70 percent of the total amount of the oxidizing agent, is added slowly into the reactor over the period of 2-4 hours while the temperature of the contents in the reactor is maintained at or lower than about 120° C. (248° F.). The minor portion (the remaining quantity) of the oxidizing agent is then quickly introduced into the reactor to accelerate the reaction rate and drive the reaction to completion. The contents in the reactor are allowed to cool to about 75° C. and maintained at this temperature until the pH value is within a range of about 4.2 to about 4.7. The resulting product is the amine-oxide surfactant of Formula I. Distilled or deionized water can then be introduced into the reactor to obtain an aqueous amine-oxide surfactant content in the range of about 50 to about 80 wt % based on the total weight of the surfactant solution.

When the $R_1$ group of the tertiary amine surfactants of Formula II is longer than 12 carbons, for example, as in ethoxylated tallowamines, the resulting amine-oxide surfactants are very viscous. A conventional viscosity reducing agent can be admixed with the amine-oxide surfactant to reduce its viscosity and thus improve its handling. Representative viscosity reducing agents include glycerol, ethylene glycol, propylene glycol, and polyethyelene glycol or polypropylene glycol having an average molecular weight of about 200 to about 1000, the like, and mixtures thereof.

The viscosity reducing agent can be internally contained in the tertiary amine surfactants, or can be added prior, during, or after the oxidation process. The viscosity reducing agent is preferably present in the surfactant solution in an amount in the range of about 1 to about 25 wt % based on the total weight of the surfactant solution.

Conventional preservatives having antimicrobial activity can be admixed with the amine-oxide surfactant. Representative preservatives include methyl paraben, propyl paraben, formaldehyde, Kathon CG/ICP [a commercially available preservative containing 1.5 wt % of the active ingredients 5-chloro-2-methyl-4-isothiazolin-3-one and 2-methyl-4-isothiazolin-3-one and 98.5 wt % of inert ingredients], the like and mixtures thereof.

The preservative is preferably present in the surfactant solution in an amount in the range of about 0.05 to about 0.15 wt % based on the total weight of the surfactant solution.

Representative agriculturally acceptable pesticides include:

FUNGICIDES AND BACTERICIDES

Carbamate fungicides such as 3,3'-ethylenebis (tetrahydro-4,6-dimethyl-2H-1,3,5-thiadiazine-2-thione), zinc or manganese ethylenebis(dithiocarbamate), bis(-dimethyldithiocarbamoyl)disulfide, zinc propylenebis (dithiocarbamate), bis(dimethyldithiocarbamoyl) ethylenediamine; nickel dimethyldithiocarbamate, methyl-1(butylcarbamoyl)-2-benzimidazolecarbamate, 1,2-bis(3-methoxycarbonyl-2-thioureido)benzene, 1-isopropylcarbamoyl-3-(3,5-dichlorophenyl)hydrate, potassium N-hydroxymethyl-N-methyldithiocarbamate and 5-methyl-10-butoxycarbonylamino-10,11-dihydrodibenzo (b,f)azepine; pyridine fungicides such as zinc bis(2-hydroxy-2-(1H)pyridinethionate) and 2-pyridinethiol-1-oxide sodium salt; phosphorus fungicides such as O,O-diisopropyl S-benzylphosphorothioate and O-ethyl S,S-diphenyldithiophosphate; phthalimide fungicides such as N-(2,6-p-diethylphenyl)phthalimide and N-(2,6-diethylphenyl)-4-methylphthalimide; dicarboxyimide fungicides such as N-trichloromethylthio-4-cyclohexene-1,2-dicarboxyimide and N-tetrachloroethylthio-4-cyclohexene-1,2-dicarboxyimide; oxathine fungicides such as 5,6-dihydro-2-methyl-1,4-oxathine-3-carboxanilido-4,4-dioxide and 5,6-dihydro-2-methyl-1,4-oxathine-3-carboxanilide; naphthoquinone fungicides such as 2,3-dichloro-1,4-naphthoquinone, 2-oxy-3-chloro-1,4-naphthoquinone copper sulfate; pentachloronitrobenzene; 1,4-dichloro-2,5-dimethoxybenzene; 5-methyl-s-triazol(3,4-b)benzthiazole; 2-(thiocyanomethylthio) benzothiazole; 3-hydroxy-5-methylisooxazole; N-2,3-dichlorophenyltetrachlorophthalamic acid; 5-ethoxy-3-trichloromethyl-1,2,4-thiadiazole; 2,4-dichloro-6-(O-chloroanilino)-1,2,5-triazine; 2,3,-dicyano-1,4-dithioanthraquinone; copper 8-quinolinate; polyoxine; validamycine; cycloheximide; sodium methanearsonate; diisopropyl 1,3-dithioloane-2-iridene malonate; 3-allyloxy-1,2-benziosothiazol-1, 1-dioxide; kasugamycin; Blasticidin S; 4,5,6,7-tetrachlorophthalide; 3-(3,5-dichlorophenyl) 5-ethenyl-5-methyloxazolizine-2,4-dione; N-3,5-dichlorophenyl)-1,2-dimethylcyclopropane-1,2-dicarboxyimide; S-n-butyl-5'-para-t-butyl-benzyl-N-3-pyridyldithiocarbonylimidate; 4-chlorophenoxy-3,3-dimethyl-1-(1H,1,3,4-triazol-1-yl)-2-butanone; methyl-D,L-N-(2,6-dimethylphenyl)-N-(N'-methoxyacetyl)alaninate; N-propyl-N-(2-(2,4,6-trichlorophenoxy) ethylimidazol-1-carboxamide; N-3,5-dichlorophenyl succinamide; tetrachloroisophthalonitrile; 2-dimethylamino-4-methyl-5-n-butyl-6-hydroxypyrimidine; 2,6-dichloro-4-nitroaniline; 3-methyl-4-chlorobenzthiazol-2-one; 1,2,5,6-tetrahydro-4H-pyrrolol[3,2,1-i,j]quinoline-2-one; 3'-isopropoxy-2-methylbenzanilide; 1-[2-(2,4-dichlorophenyl)-4-ethyl-1-3-dioxorane-2-ylmethyl) hyl]-1H,1,2,4-triazol; 1,2-benzisothiazoline-3-one; basic copper chloride; basic copper sulfate; N'-dichloroflouromethylthio-N,N-dimethyl-N-phenyl sulfamide; ethyl-N-(3-dimethylaminopropyl)thiocarbamate hydrochloride; piomycin; S,S-6-methylquinoxaline-2,3diyldithiocarbonate; complex of zinc and maneb; di-zinc bis(-dimethyldithiocarbamate)ethylenebis (dithiocarbamate).

PLANT GROWTH REGULATORS AND HERBICIDES

Isourea plant growth regulators such as N-methoxycarbonyl-N'-methylphenylcarbamoylethylisourea and 1-(4-chlorophenylcarbamoyl)-3-ethoxycarbonyl-2-methylisourea; other type of plant growth regulators such as sodium naphthaleneacetate, 1,2-dihydropyridazine-3,-6-dione and gibberellins; triazine herbicides such as 2-methylthio-4,6-bisethylamino-1,3,5-triazine, 2-chloro-4,6-bisethylamino-1,3,5-triazine, 2-methoxy-4-ethylamino-6-isopropylamino-1,3,5-triazine, 2-chloro-4-ethylamino-6-isopropylamino-S-triazine, 2-methylthio-4,6-bis(isopropylamino)-S-triazine and 2-methylthio-4-ethylamino-6-isopropylamino-s-triazine; phenoxy herbicides such as 2,4-dichlorophenoxyacetic acid and methyl, ethyl, and butyl esters thereof. 2-chloro-4-methylphenoxyacetic acid, 4-chloro-2-methylphenoxyacetic acid and ethyl 2-methyl-4-chlorophenoxybutylate; diphenylether herbicides such as 2,4,6-trichlorophenyl-4'-nitrophenylether, 2,4-dichlorophenyl-4'-nitrophenylether and 3,5-dimethylphenyl-4'-nitrophenylether; urea herbicides such as 3-(3,4-dichlorophenyl)-1-methoxy-1-methyl urea, 3-(3,4-dichlorophenyl)-1,1-dimethylurea and 3-(4-chlorophenyl)-1,1-dimethyl urea; carbamate herbicides such as 3-methoxycarbonylaminophenyl-N-(3-methylphenyl)carbamate, isopropyl-N-(3-chlorophenyl)carbamate and methyl-N-(3,4'-dichlorophenyl)carbamate; uracil herbicides such as 5-bromo-3-sec-butyl-6-methyluracil and 1-cyclohexyl-3,5-propyleneuracil; thiocarbamate herbicides such as S-(4-chlorobenzyl)-N,N-diethylthiocarbamate, S-ethyl-N-cyclohexyl-N-ethylthiocarbamate and S-ethyl-hexahydro-1H-azepine-1-carbothioate and S-ethyl-N,N-di-n-propylthiocarbamate; pyridinium herbicides such as 1,1'-di-methyl-4,4'-bispyridinium dichloride; phosphoric herbicides such as N-(phosphonomethyl)glycine; aniline herbicides such as alpha, alpha, alpha-trifluoro-2,6-dinitro-N,N-dipropyl-p-toluidine, 4-(methylsulfonyl)-2,6-dinitro-N,N-dipropylaniline and K<3>, N<3>-diethyl-2,4-dinitro-6-triflouromethyl-1,2,3-phenylene diamine; acid anilide herbicides such as 2-chloro-2',6'-diethyl-N-(butoxymethyl)acetonalide, 2-chloro-2',6'-diethyl-N(methoxymethyl)acetonalide, and 3,4-dichloropropioneanilide; pyrazlle herbicides such as 1,3-dimethyl-4-(2,4-dichlorobenzoyl)-5-hydroxypyrazole and 1,3-di-methyl-4-(2,4-dichlorobenzyol)-5-(p-toluenesulfonyloxy)pyrazole; 5-tert-butyl-3-(2,4-dichloro-5-isopropoxyphenyl)-1,3,4-oxadiazoline-2-one; 2[N-isopropyl,N-(4-chlorophenyl)carbamoyl]-4-chloro-methyl-4-isooxazoline-3-one; 3-isopropylbenzo-2-thio-1,3-diazinone-(4-2,4-dioxide) and 3-(2-methylphenoxy)pyridazine.

INSECTICIDES

Phosphoric insecticides such as O,O-diethyl 0-(2-isopropyl-4-methyl-6-pyrimidinyl) phosphorothioate, O,O-diethyl S-2-[(ethylthio)ethyl]phosphorodithioate, O,O-dimethyl O-(3-methyl-4-nitrophenyl)thiophosphate, O,O-dimethyl S-(N-methylcarbamoylmethyl)-phosphorodithioate, O,O-dimethyl S-(N-methyl-N-formylcarbamoylmethyl)phosphorodithioate, O,O-dimethyl S-2-[(ethylthio)ethyl]phosphorodithioate, O,O-diethyl S-2-diethyl S-2-[(ethylthio)-ethyl]phosphorodithioate, O,O-dimethyl-1-hydroxy-2,2,2-trichloroethylphosphonate, O,O-diethyl-O-(5-phenyl-3-isooxyazolyl)phosphorothioate, O,O-dimethyl O-(2,5-dichloro-4-bromophenyl)phosphorothioate, O,O-dimethyl 0-(3-methyl-4-methylmercaptophenyl)thiophosphate, O-ethyl O-p-cyanophenyl phenylphosphorothioate, O,O-dimethyl-S-(1,2-dicarboethoxyethyl)phosphorodithioate, 2-chloro-(2,4,5-trichlorophenyl)vinyldimethyl phosphate, 2-chloro-1-(2,4-dichlorophenyl)vinyldimethyl phosphate, O,O- dimethyl O-p-cyanophenyl phosphorothioate, 2,2-dichlorovinyl dimethyl phosphate, O,O-diethyl 0-2,4-dichlorophenyl phosphorothioate, ethyl mercaptophenylacetate O,O-dimethyl phosphorodithioate, S-[(6-chloro-2-oxo-3-benzooxyazolinyl)methyl]O,O-diethyl phosphorodithioate, 2-chloro-(2,4-dichlorophenyl)vinyl diethylphosphate O,O-diethyl 0-(3-oxo-2-phenyl-2H-pyridazine-6-yl)phosphorothioate, O,O-dimethyl S-(1-methyl-2-ethylsulfinyl)-ethyl phosphorothioate, O,O-dimethyl S-phthalimidomethyl phosphorodithioate, O,O-diethyl 2,2,2-trichloroethanol, 2-(p-tert-butylphenoxy)isopropyl-2'-chloroethylsulfite, azooxybenzene,di-(p-chlorophenyl)-cyclopropyl carbinol, di[tri(2,2-dimethyl-2-phenylethyl)tin]oxide. 1-(4-chlorophenyl)-3-(2,6-difluorobenzoyl)urea and S-tricyclohexyltin O,O-diisopropylphosphorodithioate.

INSECT REPELLENTS

The following insect repellents may be employed herein: 2-ethyl-1,3-hexanediol; N-octyl bicycloheptene dicarboximide; N,N-diethyl-M-toluamide; 2,3,4,5-Bis(2-butylene)tetrahydro-2-furaldehyde; di-n-propyl isocinchomeronate; and 2-hydroxyethyl-n-octyl sulfide.

Also useful herein are N-phosphonomethylglycines and salts thereof such as:
  mono-isopropylamine salt of N-phosphonomethyl glycine;
  mono-dimethylamine salt of N-phosphonomethyl glycine;
  mono-ethanolamine salt of N-phosphonomethyl glycine;
  mono-ammonium salt of N-phosphonomethyl glycine;
  mono-butylamine) salt of N-phosphonomethyl glycine;
  mono(methylamine) salt of N-phosphonomethyl glycine;
  monosodium salt of N-phosphonomethyl glycine;
  disodium salt of N-phosphonomethyl glycine;
  trisodium salt of N-phosphonomethyl glycine; and
  N-phosphonomethyl glycine.

Herbicides are preferred pesticides. Representative herbicides include N-(phosphonomethyl)glycine, 2,4-dichlorophenoxylacetic acid, 2-methoxy-3,6-dichlorobenzoic acid, and the salts thereof.

An aqueous agricultural composition of the present invention can comprise an agriculturally acceptable pesticide admixed with the amine-oxide surfactant of Formula I. This composition exhibits reduced irritation and reduced corrosion as compared to conventional agricultural compositions.

The agricultural composition can be diluted with water to obtain a solids concentration of about 50 to about 80 wt %.

The weight ratio of the agricultural compound to the amine-oxide surfactant of Formula I is preferably in the range of about 1:1 to about 5:1, preferably in the range of about 1:5 to about 4:1.

The present invention also includes a method of treating plants by applying thereto the aqueous agricultural composition. The plants are treated with a dose of agricultural composition effective to achieve the desired result, e.g., when the agriculturally acceptable pesticide is used, phytotoxicity is achieved.

The compositions of this invention are extremely useful in minimum tillage methods of crop culture. Thus, for example, in those instances where it is desirable to plant a sodded or otherwise vegetated acreage with corn or the like without plowing or otherwise mechanically preparing a seed bed, the crop seed can be drill planted in combination with a prior or subsequent application of a composition of this invention to kill undesired growing vegetation provided that the composition is applied before the emergence of the crop plant.

The compositions of this invention are also useful in sod (turf, alfalfa, pasture, etc.) renovation or conversion procedures. Thus, for example, in situations where a sod or parts thereof has become overgrown with undesirable plant species, the plants in said area can be sprayed with a phytotoxic composition of this invention to control all growing plants and from about 2 to 24 hours later depending upon weather conditions etc., the desired species can be seeded into the dying vegetation. Where a seed bed is to be prepared about 2 to 3 weeks should elapse between treatment and seed bed preparation, in order to provide sufficient time for the composition to be absorbed by all parts of the undesired plants. In an alternate method of sod renovation, the area can be seeded and immediately sprayed with a composition of this invention. In either method, the seeds fall among the vegetation and as the sprayed plants wither, and die, they act as a mulch and moisture retaining layer in which the seeds can germinate. This method is particularly useful in the spot renovation of lawns or golf greens or fairways since the herbicidal effect of the compositions of this invention is greatly decreased or totally inactivated by contact with soil. Thus, seeds which are in the soil can germinate and grow without any apparent effects from the spraying of the unwanted plants prior to the time that the seed actually germinates.

The compositions of this invention provide a wide spectrum of weed control and are also extremely useful as general herbicides as well as in controlling unwanted plants in orchards, tree farms, and various crops. For example, it has been found that by directing a spray of the compositions of this invention at the unwanted plants while essentially preventing such spray from contacting the leaves of trees, such unwanted plants are controlled while there is no apparent injury to the trees. In such directed spraying, the spray can fall on the woody portion of the fruit tree or other tree without any apparent effect. Thus, the directed spray method of control is useful with crops such as plantation crops, i.e. rubber, coffee, bananas, tea, etc. and in orchards such as citrus fruits, apples, peaches, pears, nuts, olive, in vineyards and in bramble crops and in nursery crops to control the undesired plants; and in crops such as cotton, soybeans, sugar cane and the like.

The compositions of this invention are also useful for control of weeds between cropping seasons, for the renovation of stale seed beds and the like.

In applying the compositions of this invention to the plants which it is desired to control, it has been found to be desirable that the plant be emerged from the ground and even more desirable, that the plant be at least at the 2-leaf stage for maximum effect. It has been found that when the plants to be controlled have a portion of their growth above the ground or water, and the aboveground or above-water portion of the plant contacted with the herbicidal compositions of this invention at appropriate rates, the herbicide is translocated to kill such plant parts which are below the ground or water surface.

One can obtain limited selectivity in crops such as cotton, soybeans, sugar cane and like crops by directing the spraying of a composition of this invention at a selected concentration on vegetation around the base of such plants with minimal spray contact with the leafy portions of such crop plants. The directed spraying can be done with or without a protective device to prevent contact of the spray with the leaves of such crop plants.

The application of an effective amount of the compounds of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.01 to about 20 or more pounds per are. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

The compositions of this invention are also useful as harvesting aids in many crops. Thus, for example, the crop could be sprayed with the compositions of this invention to reduce the bulk of unwanted material and make the harvesting of the crops easier. Such crops are for example, peanuts, soybeans, and root crops such as potatoes, sugar beets, red beets, and the like.

The following Examples are provided by way of representation of the present invention and not by way of limitation.

EXAMPLE 1

Preparation Of An Amine-Oxide Surfactant Solution From Tallowamine Ethoxylated With 15 Moles Of Ethylene Oxide A 1,000 milliliter (ml) three-necked flask equipped with an internal agitator, a heating mantle and a temperature regulator was charged with 400 grams (g) of DeSomeen TA-15 (a tallowamine ethoxylate commercially available from DeSoto, Inc. that is the condensation reaction product of one mole of tallowamine with 15 moles of ethylene oxide and that contains about 20 wt % of polyethylene glycol). Agitation was initiated and maintained throughout the preparation process. The temperature of the contents of the flask was elevated to about 90° C. Then, 40 g of hydrogen peroxide having a concentration of 50 wt % were introduced into the flask over a time period of 2 hours while maintaining the temperature of the contents of the flask in the range of about 100° to about 120° C. The temperature of the contents of the flask was maintained in the range of about 100° to about 120° C. for one hour after the completion of the addition of the hydrogen peroxide. Then, 20 g of hydrogen peroxide having a concentration of 50 wt % were quickly introduced into the flask. The contents of the flask were slowly cooled to a temperature of about 75° C. After a time period of 2 hours, the pH value of the contents of the flask was 4.5. Then, 50 g of deionized water were introduced into the flask. Agitation was discontinued 15 minutes after the deionized water had been introduced into the flask. A total of 500 g of an aqueous amine-oxide surfactant solution having 80 wt % of the amine-oxide surfactant of Formula I was produced. The yield was 98.42% based on the activity, i.e., the amine concentration, of the starting material.

Conversion of the tallowamine ethoxylate into the amine-oxide surfactant of Formula I and the structure and purity of the amine-oxide surfactant of Formula I were confirmed by the following chemical and instrumental analyses:

the pH value changed from a pH value in the range of 9 to 11, which indicate the presence of a free amine to a pH value in the range of 4.2 to 4.7, which indicates a totally oxidized amine;

results from the analysis by Proton and Carbon 13 Nuclear Magnetic Spectroscopy confirmed not only the structure of the product, but also its purity, i.e., the starting material was not detected on the spectra of the product; and when the product was heated to about 150° C. for a prolonged time period it decomposed to yield the products of the typical Cope elimination reaction of an amine-oxide. The Cope elimination reaction is described in March, Id., p. 909.

EXAMPLE 2

Preparation Of An Amine-Oxide Surfactant Solution From Tallowamine Ethyoxylated With 20 Moles Of Ethylene Oxide The experiment of EXAMPLE 1 was repeated utilizing the same equipment and reaction parameters but replacing the DeSomeen TA-15 with an equal amount of DeSomeen TA-20 (a surfactant commercially available from DeSoto, Inc. that is the condensation reaction product of one mole of tallowamine and 20 moles of ethylene oxide and that contains about 20% wt % of polyethylene glycol) and utilizing a total of 50 g of hydrogen peroxide having a concentration of 50 wt %. The resulting amine-oxide surfactant solution exhibited the same pH value, purity, and Cope elimination reaction as the surfactant solution of EXAMPLE 1. The yield was 98.9% based on the activity of the starting material.

EXAMPLE 3

Preparation Of An Amine-Oxide Surfactant Solution From Tallowamine Ethoxylated With 10 Moles Of Ethylene Oxide The experiment of EXAMPLE 1 was repeated utilizing the same equipment and reaction parameters but replacing the DeSomeen TA-15 with an equal amount of DeSomeen TA-10 (a surfactant commercially available from DeSoto, Inc. that is the condensation reaction product of one mole of tallowamine and 10 moles of ethylene oxide and that contains about 15% wt % of polyethylene glycol) and utilizing a total of 75 g of hydrogen peroxide having a concentration of 50 wt %. The resulting amine-oxide surfactant solution exhibited the same pH value, purity, and Cope elimination reaction as the surfactant solution of EXAMPLE 1. The yield was 99.1% based on the activity of the starting material.

EXAMPLE 4

Preparation Of An Amine-Oxide Surfactant Solution From Tallowamine Ethyoxylated With 20 Moles Of Ethylene Oxide And 4 Moles Of Propylene Oxide The experiment of EXAMPLE 1 was repeated utilizing the same equipment and reaction parameters but replacing the DeSomeen TA-15 with an equal amount of FloMo 1513 (a surfactant commercially available from DeSoto, Inc. that is the condensation reaction product of one mole of tallowamine and 20 moles of ethylene oxide followed by the condensation reaction therewith of 4 moles of propylene oxide and that contains about 20 wt % of polyethylene glycol) and utilizing a total of 60 g of hydrogen peroxide having a concentration of 50 wt %. The resulting amine-oxide surfactant solution exhibited substantially the same pH value, purity, and Cope elimination reaction as the surfactant solution of EXAMPLE 1. The yield was 98.5% based on the activity of the starting material.

EXAMPLE 5

Preparation Of An Amine-Oxide Surfactant Solution From Laurylamine Ethoxylate The experiment of EXAMPLE 1 was repeated utilizing the same equipment and reaction parameters but replacing the DeSomeen TA-15 with an equal amount of DeSomeen LA-16.5 (a surfactant commercially available from DeSoto, Inc. that is the condensation reaction product of one mole of laurylamine and 16.5 moles of ethylene oxide) and utilizing a total of 75 g of hydrogen peroxide having a concentration of 50 wt %. The resulting amine-oxide surfactant solution product exhibited substantially the same pH value, purity, and Cope elimination reaction as the surfactant solution of EXAMPLE 1. The yield was 99.0% based on the activity of the starting material.

EXAMPLE 6

Preparation Of An Amine-Oxide Surfactant Solution From Hydrogenated Tallowamine Ethoxylate The experiment of EXAMPLE 1 was repeated utilizing the same equipment and reaction parameters but replacing the DeSomeen TA-15 with an equal amount of Varonic U215 (a surfactant commercially available from Sherex that is the condensation reaction product of one mole of hydrogenated tallowamine and 15 moles of ethylene oxide) and utilizing a total of 75 g of hydrogen peroxide having a concentration of 50 wt %. The amine-oxide surfactant was admixed with 200 g of deionized water and 150 g of polyethylene glyclo having average molecular weight of 300 to obtain a surfactant solution having about 50 wt % of the amine-oxide surfactant. The resulting amine-oxide surfactant solution exhibited substantially the same pH value, purity, and Cope elimination reaction as the surfactant solution of EXAMPLE 1. The yield was 98.3% based on the activity of the starting material.

EXAMPLE 7

Preparation Of An Amine-Oxide Surfactant Solution From Cocoamine Ethoxylate

The experiment of EXAMPLE 1 was repeated utilizing the same equipment and reaction parameters but replacing the DeSomeen TA-15 with an equal amount of Varonic K215 (a surfactant commercially available from Sherex that is the condensation reaction product of one mole of cocoamine and 15 moles of ethylene oxide) and utilizing a total of 75 g of hydrogen peroxide having a concentration of 50 wt %. The resulting amine-oxide surfactant solution exhibited the same pH value, purity, and Cope elimination reaction as the surfactant solution of EXAMPLE 1. The yield was 99.1% based on the activity of the starting material.

EXAMPLE 8

Preparation Of Amine-Oxide Surfactant Solution Utilizing Hydrogen Peroxide Having A Concentration Of 35 Weight Percent EXAMPLE 1 was repeated using scale-up quantities but hydrogen peroxide having a concentration of 35 wt %, which is a lower strength oxidizing reagent, was utilized in place of hydrogen peroxide having a concentration of 50 wt %. The yield was about 98.9% based on the activity of the starting material.

The results of this Example confirm that oxidizing reagents of lesser strength can be utilized to produce the amine-oxide surfactants of Formula I. However, larger quantities of the lower strength oxidizing reagents and longer time periods, as compared to when a stronger oxidizing reagent is utilized, are required to obtain the desired yield and an amine-oxide surfactant of Formula I having the same properties.

EXAMPLE 9

Eye-Irritation Test

The amine-oxide surfactants produced in EXAMPLES 1 to 5, a control of N-(2-hydroxyethyl)-acetamide (control A), a known non-irritant, and an ethoxylated tallow amine (FloMo$^R$ TD-20) (control B) were tested for eye-irritation in accordance with the Consumer Product Safety Commission, Volume 36, Number 187, Part II, Test No. 1500.42. In this test, one-tenth milliliter of each amine-oxide surfactant or the control was placed in the eyes of six rabbits. The cornea, iris and conjunctiva of the eyes were observed after 24, 48 and 72 hours of exposure. Results of the tests confirmed that all of the amine-oxide surfactants of EXAMPLES 1 to 5 are not eye irritants.

The following scoring table for eye table for eye irritation grades for ocular lesions was used:

| Cornea | |
|---|---|
| No ulceration or opacity | 0 |
| Scattered or diffused areas of opacity (other than slight dulling of normal luster), details of iris clearly visible. | 1 |
| Easily discernible translucent area, details of iris slightly obscured. | 2 |
| Nacreous areas, no details of iris visible, size of pupil barely discernible | 3 |
| Iris | |
| Normal | 0 |
| Markedly deepened folds, congestion, swelling, moderate circumcorneal injection (any of these or a combination of any thereof), iris still reacting to light (sluggish reaction is positive) | 1 |
| No reaction to light, hemorrhage, gross destruction (any or all of these) | 2 |
| Conjunctiva Redness (refers to the palpebral and bulbar conjunctivae excluding the cornea and iris) | |
| Vessels normal | 0 |
| Some vessels definitely injected | 1 |
| Diffuse, crimson red, individual vessels not easily discernible | 2 |
| Diffuse, beefy red | 3 |

Chemosis

| | |
|---|---|
| No swelling | 0 |
| Any swelling above normal (includes nictitating membrane) | 1 |
| Obvious swelling with partial eversion of lids | 2 |
| Swelling with lids about half closed | 3 |
| Swelling with lids more than half closed | 4 |

TABLE 1

Control A

| Rabbit Number | | 1 | | | 2 | | | 3 | |
|---|---|---|---|---|---|---|---|---|---|
| Hours After Treatment | 24 | 48 | 72 | 24 | 48 | 72 | 24 | 48 | 72 |
| Cornea | 0 | 0 | 0 | 0 | 0 | 0 | 0 | 0 | 0 |
| Iris | 0 | 0 | 0 | 0 | 0 | 0 | 0 | 0 | 0 |
| Conjunctiva: Erythema | 1 | 0 | 0 | 0 | 0 | 0 | 0 | 0 | 0 |
| Chemosis | 0 | 0 | 0 | 0 | 0 | 0 | 0 | 0 | 0 |

| Rabbit Number | | 1 | | | 2 | | | 3 | |
|---|---|---|---|---|---|---|---|---|---|
| Hours After Treatment | 24 | 48 | 72 | 24 | 48 | 72 | 24 | 48 | 72 |
| Cornea | 0 | 0 | 0 | 0 | 0 | 0 | 0 | 0 | 0 |
| Iris | 0 | 0 | 0 | 0 | 0 | 0 | 0 | 0 | 0 |
| Conjunctiva: Erythema | 0 | 0 | 0 | 1 | 0 | 0 | 1 | 0 | 0 |
| Chemosis | 0 | 0 | 0 | 0 | 0 | 0 | 0 | 0 | 0 |

TABLE 2

Control B

| Rabbit Number | | 1 | | | 2 | | | 3 | |
|---|---|---|---|---|---|---|---|---|---|
| Hours After Treatment | 24 | 48 | 72 | 24 | 48 | 72 | 24 | 48 | 72 |
| Cornea | 1 | 2 | 2 | 1 | 1 | 2 | 1 | 2 | 2 |
| Iris | 1 | 1 | 1 | 1 | 1 | 1 | 1 | 1 | 1 |
| Conjunctiva: Erythema | 2 | 2 | 2 | 2 | 2 | 2 | 2 | 2 | 2 |
| Chemosis | 3 | 3 | 3 | 3 | 3 | 3 | 3 | 3 | 2 |

| Rabbit Number | | 1 | | | 2 | | | 3 | |
|---|---|---|---|---|---|---|---|---|---|
| Hours After Treatment | 24 | 48 | 72 | 24 | 48 | 72 | 24 | 48 | 72 |
| Cornea | 1 | 2 | 2 | 1 | 1 | 2 | 1 | 2 | 2 |
| Iris | 1 | 1 | 1 | 1 | 1 | 1 | 1 | 1 | 2 |
| Conjunctiva: Erythema | 2 | 2 | 2 | 2 | 2 | 2 | 2 | 2 | 2 |
| Chemosis | 3 | 3 | 2 | 2 | 2 | 2 | 3 | 3 | 3 |

TABLE 3

Product of Example 1

| Rabbit Number | | 1 | | | 2 | | | 3 | |
|---|---|---|---|---|---|---|---|---|---|
| Hours After Treatment | 24 | 48 | 72 | 24 | 48 | 72 | 24 | 48 | 72 |
| Cornea | 0 | 0 | 0 | 0 | 0 | 0 | 0 | 0 | 0 |
| Iris | 0 | 0 | 0 | 0 | 0 | 0 | 0 | 0 | 0 |
| Conjunctiva: Erythema | 2 | 2 | 1 | 1 | 1 | 1 | 1 | 1 | 1 |
| Chemosis | 2 | 1 | 1 | 1 | 0 | 0 | 1 | 1 | 1 |

| Rabbit Number | | 1 | | | 2 | | | 3 | |
|---|---|---|---|---|---|---|---|---|---|
| Hours After Treatment | 24 | 48 | 72 | 24 | 48 | 72 | 24 | 48 | 72 |
| Cornea | 0 | 0 | 0 | 0 | 0 | 0 | 0 | 0 | 0 |
| Iris | 0 | 0 | 0 | 0 | 0 | 0 | 0 | 0 | 0 |
| Conjunctiva: Erythema | 1 | 1 | 0 | 1 | 1 | 0 | 1 | 1 | 0 |
| Chemosis | 0 | 0 | 0 | 0 | 0 | 0 | 0 | 0 | 0 |

TABLE 4

Product of Example 2

| Rabbit Number | | 1 | | | 2 | | | 3 | |
|---|---|---|---|---|---|---|---|---|---|
| Hours After Treatment | 24 | 48 | 72 | 24 | 48 | 72 | 24 | 48 | 72 |
| Cornea | 0 | 0 | 0 | 0 | 0 | 0 | 0 | 0 | 0 |
| Iris | 0 | 0 | 0 | 0 | 0 | 0 | 0 | 0 | 0 |
| Conjunctiva: Erythema | 1 | 1 | 0 | 0 | 0 | 0 | 1 | 0 | 0 |
| Chemosis | 0 | 0 | 0 | 0 | 0 | 0 | 0 | 0 | 0 |

| Rabbit Number | | 1 | | | 2 | | | 3 | |
|---|---|---|---|---|---|---|---|---|---|
| Hours After Treatment | 24 | 48 | 72 | 24 | 48 | 72 | 24 | 48 | 72 |
| Cornea | 0 | 0 | 0 | 0 | 0 | 0 | 0 | 0 | 0 |
| Iris | 0 | 0 | 0 | 0 | 0 | 0 | 0 | 0 | 0 |
| Conjunctiva: Erythema | 0 | 0 | 0 | 1 | 1 | 0 | 1 | 1 | 0 |
| Chemosis | 0 | 0 | 0 | 0 | 0 | 0 | 0 | 0 | 0 |

TABLE 5

Product of Example 3

| Rabbit Number | | 1 | | | 2 | | | 3 | |
|---|---|---|---|---|---|---|---|---|---|
| Hours After Treatment | 24 | 48 | 72 | 24 | 48 | 72 | 24 | 48 | 72 |
| Cornea | 0 | 0 | 0 | 0 | 0 | 0 | 0 | 0 | 0 |
| Iris | 0 | 0 | 0 | 0 | 0 | 0 | 0 | 0 | 0 |
| Conjunctiva: Erythema | 2 | 2 | 1 | 1 | 1 | 0 | 2 | 1 | 1 |
| Chemosis | 2 | 1 | 1 | 1 | 1 | 0 | 1 | 1 | 0 |

| Rabbit Number | | 1 | | | 2 | | | 3 | |
|---|---|---|---|---|---|---|---|---|---|
| Hours After Treatment | 24 | 48 | 72 | 24 | 48 | 72 | 24 | 48 | 72 |
| Cornea | 0 | 0 | 0 | 0 | 0 | 0 | 0 | 0 | 0 |
| Iris | 0 | 0 | 0 | 0 | 0 | 0 | 0 | 0 | 0 |
| Conjunctiva: Erythema | 1 | 1 | 1 | 1 | 1 | 0 | 1 | 1 | 0 |
| Chemosis | 1 | 1 | 0 | 1 | 0 | 0 | 1 | 0 | 0 |

TABLE 6

Product of Example 4

| Rabbit Number | | 1 | | | 2 | | | 3 | |
|---|---|---|---|---|---|---|---|---|---|
| Hours After Treatment | 24 | 48 | 72 | 24 | 48 | 72 | 24 | 48 | 72 |
| Cornea | 0 | 0 | 0 | 0 | 0 | 0 | 0 | 0 | 0 |
| Iris | 0 | 0 | 0 | 0 | 0 | 0 | 0 | 0 | 0 |
| Conjunctiva: Erythema | 1 | 1 | 0 | 1 | 0 | 0 | 1 | 0 | 0 |
| Chemosis | 0 | 0 | 0 | 0 | 0 | 0 | 0 | 0 | 0 |

| Rabbit Number | | 1 | | | 2 | | | 3 | |
|---|---|---|---|---|---|---|---|---|---|
| Hours After Treatment | 24 | 48 | 72 | 24 | 48 | 72 | 24 | 48 | 72 |
| Cornea | 0 | 0 | 0 | 0 | 0 | 0 | 0 | 0 | 0 |
| Iris | 0 | 0 | 0 | 0 | 0 | 0 | 0 | 0 | 0 |
| Conjunctiva: Erythema | 1 | 0 | 0 | 0 | 0 | 1 | 1 | 0 | 0 |
| Chemosis | 0 | 0 | 0 | 0 | 0 | 0 | 0 | 0 | 0 |

TABLE 7

Product of Example 5

| Rabbit Number | | 1 | | | 2 | | | 3 | |
|---|---|---|---|---|---|---|---|---|---|
| Hours After Treatment | 24 | 48 | 72 | 24 | 48 | 72 | 24 | 48 | 72 |
| Cornea | 0 | 0 | 0 | 0 | 0 | 0 | 0 | 0 | 0 |
| Iris | 0 | 0 | 0 | 0 | 0 | 0 | 0 | 0 | 0 |
| Conjunctiva: Erythema | 0 | 0 | 0 | 0 | 0 | 0 | 0 | 0 | 0 |
| Chemosis | 0 | 0 | 0 | 0 | 0 | 0 | 0 | 0 | 0 |

| Rabbit Number | | 1 | | | 2 | | | 3 | |
|---|---|---|---|---|---|---|---|---|---|
| Hours After Treatment | 24 | 48 | 72 | 24 | 48 | 72 | 24 | 48 | 72 |
| Cornea | 0 | 0 | 0 | 0 | 0 | 0 | 0 | 0 | 0 |
| Iris | 0 | 0 | 0 | 0 | 0 | 0 | 0 | 0 | 0 |
| Conjunctiva: Erythema | 0 | 0 | 0 | 1 | 0 | 0 | 0 | 0 | 0 |
| Chemosis | 0 | 0 | 0 | 0 | 0 | 0 | 0 | 0 | 0 |

EXAMPLE 10

Preparation Of Aqueous Herbicide Compositions

Aqueous herbicide compositions A, B and C were prepared utilizing the amine-oxide surfactant of EXAMPLE 1, 2 or 3, respectively. These herbicide compositions were produced by charging a suitable flask having an agitator with 65 parts by weight (pbw) of the herbicidally active composition N-(phosphonomethyl)glycine, isopropylamine salt (an aqueous solution having 62 wt % solids). Agitation was initiated and maintained throughout the preparation. A charge of 20 pbw of deionized water was introduced into the flask. Fifteen minutes after the introduction of the water a clear solution was obtained. Then, 15 pbw of the amine-oxide surfactant of EXAMPLE 1, 2 or 3 was introduced into the flask over a time period of 5 minutes. Agitation was discontinued 15 minutes after the completion of the introduction of the amine-oxide surfactant to produce an aqueous herbicide composition.

EXAMPLE 11

Preparation Of Aqueous Herbicide Composition D

Aqueous herbicide composition D was prepared utilizing a suitable flask having an agitator into which was introduced 20 pbw of the herbicidally active composition N-(phosphonomethyl)glycine, isopropylamine salt (an aqueous solution having 62 wt % solids) and 22 pbw of the herbicidally active composition 2,2-dichlorophenoxylacetic acid, isopropylamine salt (an aqueous solution having 53 wt % solids). Agitation was initiated and maintained throughout the preparation. A charge of 45 pbw of deionized water was introduced into the flask. Fifteen minutes after the introduction of the water a clear solution was obtained. Then, 13 pbw of the amine-oxide surfactant of EXAMPLE 1 was introduced into the flask over a time period of about 5 minutes. Agitation was discontinued 15 minutes after the completion of the introduction of the amine-oxide surfactant to produce the aqueous herbicide composition D.

EXAMPLE 12

Preparation Of Aqueous Herbicide Composition E

Aqueous herbicide composition E was produced utilizing a stainless steel beaker equipped with an agitator into which was introduced 27 pbw of the herbicidally active composition N-(phosphonomethyl)glycine, isopropylamine salt (an aqueous solution having 62 wt % solids) and 33.5 pbw of deionized water. Agitation was initiated and maintained throughout the preparation. After a time period of 10 minutes, 18 pbw of the herbicidally active composition 2-methoxy-3,6-dichlorobenzoic acid, isopropylamine salt were introduced into the beaker. Fifteen minutes after the introduction of the isopropylamine salt of the dichlorobenzoic acid a clear solution was obtained. Then, 21.5 pbw of the amine-oxide surfactant of EXAMPLE 2 were introduced into the beaker over a time period of 5 minutes. Agitation was discontinued 15 minutes after the completion of the introduction of amine-oxide surfactant to produce the aqueous herbicide composition of E.

EXAMPLE 13

Test For Efficacy Of The Herbicide Compositions

Aliquots of herbicide compositions A, B and C prepared in EXAMPLE 11 were tested to evaluate their efficacy. Control herbicide compositions A and B were prepared in accordance with the procedure of EXAMPLE 11 with the amine-oxide surfactant being replaced with an equal amount of either DeSomeen TA-20 to produce control herbicide composition A or N-(2-hydroxyethyl) acetamide to produce control herbicide composition B.

Herbicide compositions A to C and controlled herbicide compositions A and B were then diluted with deionized water at a dilution weight ratio of composition:water of 1:80. The diluted compositions were then sprayed on bermuda grass (Cynodon dactylon) at an application rate equivalent to 25 gallons of diluted composition per acre of grass.

The treated grass was observed six days after application of the diluted compositions. Phytotoxicity, manifested by burnt leaves, was observed in grass sprayed with herbicide compositions A to C and control herbicide composition A. No phytotoxicity was observed for the grass treated with control herbicide composition B. Thus, the amine-oxide surfactant does not adversely affect the herbicidal activity of the herbicidally active composition.

I claim:

1. An aqueous agricultural composition exhibiting reduced eye irritation to animals and reduced corrosiveness to metals comprising an agriculturally acceptable pesticide admixed with an amine-oxide surfactant having the Formula:

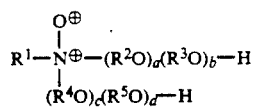

wherein $R^1$ is a straight or branched chain about $C_6$ to about $C_{20}$ alkyl or alkenyl group, $R^2$, $R^3$, $R^4$ and $R^5$ are each independently selected from the group of straight and branched chain lower alkylenyl groups and $a+b+c+d$ is about 5 to about 25.

2. The composition in accordance with claim 1 wherein $a+c$ is about 5 to about 15 and $b+d$ is 1 to about 10.

3. The composition in accordance with claim 1 wherein $R^1$ is derived from an acid selected from the group consisting of tallow acid, coconut acid, soya acid, cottonseed acid, lauric acid and stearic acid and mixtures thereof.

4. The composition in accordance with claim 1 wherein one of a and b is 0, one of c and d is 0, $R^2$, $R^3$, $R^4$, and $R^5$ are all ethylenyl groups and $a+b+c+d$ is about 5 to about 20.

5. The composition in accordance with claim 1 wherein one of a and b is 0, one of c and d is 0, $R^2$, $R^3$, $R^4$ and $R^5$ are all 1,2-propylenyl groups and $a+b+c+d$ is about 5 to about 20.

6. The composition in accordance with claim 1 wherein $R^2$ and $R^4$ are alike and are selected from the group of ethylenyl and 1,2-propylenyl, $R^3$ and $R^5$ are alike and are selected from the group of ethylenyl and 1,2-propylenyl, $a+c$ is about 5 to about 15 and $b+d$ is 1 to about 10.

7. The composition in accordance with claim 6 wherein $R^2$, $R^3$, $R^4$ and $R^5$ are alike.

8. The composition in accordance with claim 3 wherein $a+b+c+d$ is about 5 to about 20.

9. The composition in accordance with claim 1 wherein the amine-oxide surfactant is produced by oxidation of a tertiary amine surfactant having the Formula:

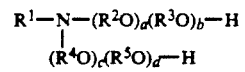

wherein $R^1$, $R^2$, $R^3$, $R^4$, $R^5$, a, b, c and d are as defined in claim 14 by reaction with a strong acid.

10. The composition in accordance with claim 9 wherein the tertiary amine surfactant is oxidized with a strong oxidizing reagent in an amount effective to oxidize about 80 to about 100 percent of the amino groups.

11. The composition in accordance with claim 9 wherein the tertiary amine surfactant is oxidized with a strong oxidizing reagent in an amount effective to oxidize about 90 to about 100 percent of the amino groups.

12. The composition in accordance with claim 1 wherein the agricultural compound is a herbicidally active compound.

13. The composition in accordance with claim 12 wherein the herbicidally active compound is selected from the group consisting of N-(phosphonomethyl)glycine, 2,4-dichlorophenoxyacetic acid, 2-methoxy-3,6-dichlorobenzoic acid and the salts thereof.

* * * * *